(12) United States Patent
Gunderson et al.

(10) Patent No.: US 10,787,704 B2
(45) Date of Patent: Sep. 29, 2020

(54) FIELD-EFFECT APPARATUS AND METHODS FOR SEQUENCING NUCLEIC ACIDS

(71) Applicants: Illumina, Inc., San Diego, CA (US); The Regents of the University of California, Oakland, CA (US)

(72) Inventors: Kevin L Gunderson, Encinitas, CA (US); Jingwei Bai, San Diego, CA (US); Cheng-Yao Chen, Eugene, OR (US); Jeffrey G Mandell, San Diego, CA (US); Sergio Peisajovich, San Diego, CA (US); Philip G Collins, Oakland, CA (US); Gregory A Weiss, Oakland, CA (US); Boyan Boyanov, San Diego, CA (US)

(73) Assignees: ILLUMINA, INC., San Diego, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 181 days.

(21) Appl. No.: 15/572,741

(22) PCT Filed: May 11, 2016

(86) PCT No.: PCT/US2016/031891
§ 371 (c)(1),
(2) Date: Nov. 8, 2017

(87) PCT Pub. No.: WO2016/183218
PCT Pub. Date: Nov. 17, 2016

(65) Prior Publication Data
US 2018/0155773 A1 Jun. 7, 2018

Related U.S. Application Data

(60) Provisional application No. 62/160,460, filed on May 12, 2015.

(51) Int. Cl.
*C12P 19/34* (2006.01)
*C12Q 1/6869* (2018.01)

(52) U.S. Cl.
CPC .................................. *C12Q 1/6869* (2013.01)

(58) Field of Classification Search
None
See application file for complete search history.

(56) References Cited

U.S. PATENT DOCUMENTS

| | | | |
|---|---|---|---|
| 6,013,456 | A | 1/2000 | Akhavan-Tafti |
| 7,057,026 | B2 | 6/2006 | Barnes et al. |
| 7,414,116 | B2 | 8/2008 | Milton et al. |
| 7,427,673 | B2 | 9/2008 | Balasubramanian et al. |
| 7,556,922 | B2 | 7/2009 | Block et al. |
| 2007/0141598 | A1 | 6/2007 | Turner et al. |
| 2010/0111768 | A1 | 5/2010 | Banerjee et al. |
| 2011/0312529 | A1 | 12/2011 | He et al. |
| 2013/0078622 | A1 | 3/2013 | Collins |
| 2013/0079232 | A1 | 3/2013 | Kain et al. |
| 2013/0165328 | A1 | 6/2013 | Previte et al. |
| 2014/0057339 | A1 | 2/2014 | Esfandyarpour |
| 2014/0329699 | A1* | 11/2014 | Esfandyarpour .. G01N 27/3278 506/6 |
| 2015/0065353 | A1 | 3/2015 | Turner |

FOREIGN PATENT DOCUMENTS

| | | |
|---|---|---|
| JP | 2014518633 | 8/2014 |
| WO | 1991/006678 | 5/1991 |
| WO | 2007/123744 | 11/2007 |
| WO | 2012/166742 | 12/2012 |
| WO | 2016010975 A2 | 1/2016 |

OTHER PUBLICATIONS

Sauer, T., Authorized Officer, European Patent Office, International Search Report and Written Opinion, International Application No. PCT/US2016/031891, dated Jul. 11, 2016, 11 pages.
Bentley et al., "Accurate whole human genome sequencing using reversible terminator chemistry" Nature, vol. 456, 53-59, 2008.
Besteman "Enzyme-Coated Carbon Nanotubes as Single-Molecule Biosensors" Nano Letters, vol. 3. (6), 727-730, 2003.
Briseno et al., "Introducing organic nanowire transistors", Materials Today; vol. 11 (4), 38-47, 2008.
Chance et al., "The accelerated flow method for rapid reactions" J. Franklin Inst 229 (5), 737, 1940.
Chen et al., "Noncovalent functionalization of carbon nanotubes for highly specific electronic biosensors" PNAS; vol. 100 (9), 4984-4989, 2003.
Chen et al., "Noncovalent Sidewall Functionalization of Single-Walled Carbon Nanotubes for Protein Immobilization" J. Am. Chem. Soc.; vol. 123 (16), 3838-3839, 2001.
Choi et al., "Dissecting Single-Molecule Signal Transduction in Carbon Nanotube Circuits with Protein Engineering" Nano Letters 13, 625-631, 2013.
Choi et al., "Single-Molecule Lysozyme Dynamics Monitored by an Electronic Circuit" Science 335, 319-324, 2012.
Cui et al., "High Performance Silicon Nanowire Field Effect Transistors" Nano Letters; vol. 3 (2) 149-152, 2003.
Goldsmith et al., "Conductance-Controlled Point Functionalization of Single-Walled Carbon Nanotubes" Science vol. 315, 77-81, 2007.

(Continued)

*Primary Examiner* — Kenneth R Horlick
(74) *Attorney, Agent, or Firm* — Illumina, Inc.

(57) ABSTRACT

The present disclosure provides a method for sequencing nucleic acids. The method can include polymerase catalyzed incorporation of nucleotides into a nascent nucleic acid strand against a nucleic acid template, wherein the polymerase is attached to a charge sensor that detects nucleotide incorporation events. One or more non-natural nucleotide types that each produce a unique signatures at the charge sensor can be used to uniquely identify different nucleotides in the template nucleic acid.

44 Claims, 10 Drawing Sheets

(56) References Cited

OTHER PUBLICATIONS

Gruner, "Carbon nanotube transistors for biosensing applications" Anal. Bioanal Chem vol. 384, 322-335, 2006.

Huang et al., "Sub 50-nm FinFET: PMOS" IEDM, 67-70, 1999.

Ionescu et al., "Tunnel field-effect transistors as energy-efficient electronic switches" Nature vol. 479, 329-337, 2011.

Krueger et al., "Redesigning the architecture of the base pair: toward biochemical and biological function of new genetic sets" Chem & Biol. 16, 242-248, 2009.

Macdiarmid, "Synthetic Metals: A Novel Role for Organic Polymers (Nobel Lecture)" Angew. Chem. Int. Ed. vol. 40, 2581-2590, 2001.

McNeill et al., "Electronic Conduction in Polymers—I. The Chemical Structure of Polypyrrole" Aust. J. Chem. vol. 16, 1056-1075, 1963.

Mohan et al., "Effect of channel length on the electrical response of carbon nanotube field-effect transistors to deoxyribonucleic acid hybridization" Beilstein Journal of Nanotechnology 5, 2081-2091, 2014.

Olsen et al., "Electronic Measurements of Single-Molecule Processing by DNA Polymerase I (Klenow Fragment)" J Am Chem Soc 135 (21), 7855-7860, 2013.

Patro et al., "Role of the 2-Amino Group of Purines during dNTP Polymerization by Human DNA Polymerase α†" Biochemistry 48 (1), 180-189, 2009.

Sarkar et al., "Proposal for tunnel-field-effect-transistor as ultra-sensitive and label-free biosensors" Appl. Phys. Lett. vol. 100, 143108, 2012.

Star et al., "Electronic Detection of Specific Protein Binding Using Nanotube FET Devices" Nano Letters vol. 3 (4), 459-463, 2003.

Star et al., "Electronic Detection of the Enzymatic Degradation of Starch" Organic Letters vol. 6 (13), 2089-2092, 2004.

Swaminathan et al., "Steep Slope Devices: Enabling New Architectural Paradigms" Proceedings of the 51st Annual Design Automation Conference on Design Automation Conference, 1-6, 2014.

Vernitskaya et al., "Polypyrrole: a conducting polymer; its synthesis, properties and applications" Russ. Chem. Rev. vol. 66, 443-457, 1997.

* cited by examiner

| Parameter | State 1 | State 2 |
|---|---|---|
| Polarity | (+) | (−) |
| Kinetics | Slow | Fast |

FIG. 7A

| Base call → | A | G | C | T |
|---|---|---|---|---|
| Polarity | (+) | (+) | (−) | (−) |
| Kinetics | Slow | Fast | Slow | Fast |

FIG. 7B

| Template | G | T | A | C | G | T | A | C | G | T | A | C | G | T | A | C | G | T | A | C | G | T | A | C |
|---|---|---|---|---|---|---|---|---|---|---|---|---|---|---|---|---|---|---|---|---|---|---|---|---|
| Run 1: modified C | | | | | | | | | | | | | | | | | | | | | | | | |
| Run 2: modified A | | | | | | | | | | | | | | | | | | | | | | | | |
| Run 3: modified T | | | | | | | | | | | | | | | | | | | | | | | | |
| Run 4: modified G | | | | | | | | | | | | | | | | | | | | | | | | |

FIG. 8A

| Base call → | A | G | C | T |
|---|---|---|---|---|
| Run 1: modified C | Low | Low | High | Low |
| Run 2: modified A | High | Low | Low | High |
| Run 3: modified T | Low | Low | Low | Low |
| Run 4: modified G | Low | High | Low | Low |

FIG. 8B

| Template | G | T | A | C | G | T | A | C | G | T | A | C | G | T | A | C | G | T | A | C | G | T | A | C | G | T | A | C |
|---|---|---|---|---|---|---|---|---|---|---|---|---|---|---|---|---|---|---|---|---|---|---|---|---|---|---|---|---|
| Run 1: modified G, C | | | | | | | | | | | | | | | | | | | | | | | | | | | | |
| Run 2: modified T, C | | | | | | | | | | | | | | | | | | | | | | | | | | | | |

FIG. 9A

| Base call → | A | G | C | T |
|---|---|---|---|---|
| Run 1: modified G,C | Low | High | High | Low |
| Run 2: modified T,C | Low | Low | High | High |

FIG. 9B

FIELD-EFFECT APPARATUS AND METHODS FOR SEQUENCING NUCLEIC ACIDS

CROSS-REFERENCE TO RELATED APPLICATIONS

The present application is a 35 U.S.C. § 371 National Stage application of International Patent Application No. PCT/US2016/031891, filed on May 11, 2016, which further claims the benefit of priority to U.S. Provisional Patent Application No. 62/160,460, filed May 12, 2015, each of which is hereby incorporated by reference in its entirety.

This invention was made with government support under grant number 1R01-GM106957 awarded by the National Institute of General Medical Sciences. The United States Government has certain rights in this invention.

BACKGROUND

This disclosure relates generally to biosensor-based detection, and more specifically to biosensors that can be used for nucleic acid sequencing.

Currently available commercial platforms for sequencing DNA are relatively costly. The majority of these platforms use a 'sequencing-by-synthesis' approach, so called because DNA polymers are synthesized while detecting the addition of each monomer (i.e. nucleotide) to the growing polymer structure. Because a template DNA strand strictly directs synthesis of a new DNA polymer, one can infer the sequence of the template DNA from the series of nucleotide monomers that were added to the growing strand during the synthesis. Monitoring the reaction uses relatively expensive hardware such as lasers, detection optics and complex fluid delivery systems. The most successful commercial platforms to date also require expensive reagents and hardware to amplify the DNA templates before sequencing-by-synthesis can even begin. The complexity and expense of these platforms has hindered their use in some clinical and research contexts where there is a clear need for DNA sequencing technology.

Thus, there exists a need for improvements to nucleic acid sequencing platforms to make them more cost effective, rapid and convenient. The present disclosure addresses this need and provides other advantages as well.

BRIEF SUMMARY

The present disclosure provides a method of nucleic acid sequencing. The method can include steps of (a) providing a polymerase attached to a solid support charge sensor; (b) contacting the polymerase with a mixture of nucleotide triphosphates, wherein the mixture includes different types of nucleotide triphosphates, wherein a first type of the nucleotide triphosphates is in a distinguishable state compared to the other types of nucleotide triphosphates in the mixture, wherein a second type of the nucleotide triphosphates is not in the distinguishable state compared to the other types of nucleotide triphosphates in the mixture, and wherein the polymerase incorporates nucleotides from the mixture into a nascent strand against a template nucleic acid strand; (c) detecting the incorporation of the nucleotides via the charge sensor, wherein the first type of the nucleotide triphosphates produces a signal that is unique compared to signals produced by other nucleotide triphosphates in the mixture, thereby acquiring a first signal pattern; (d) repeating steps (b) and (c) using the polymerase, the template nucleic acid, and a second mixture of nucleotide triphosphates, wherein the second type of the nucleotide triphosphates is in a distinguishable state compared to the other types of nucleotide triphosphates in the second mixture, and wherein the first type of the nucleotide triphosphates is not in the distinguishable state compared to the other types of nucleotide triphosphates in the second mixture, thereby acquiring a second signal pattern; and (e) comparing the first and second signal patterns to determine the sequence of the template nucleic acid.

Also provided is a method of nucleic acid sequencing that includes steps of (a) providing a polymerase attached to a solid support charge sensor; (b) contacting the polymerase with a mixture of nucleotide triphosphates, wherein the mixture includes different types of nucleotide triphosphates, wherein a first two types of the nucleotide triphosphates are in a first distinguishable state compared to a second two types of the nucleotide triphosphates in the mixture, and wherein the polymerase incorporates nucleotides from the mixture into a nascent strand against a template nucleic acid strand; (c) detecting the incorporation of the nucleotides via the charge sensor, wherein the first two types of the nucleotide triphosphates produce a signal that distinguished from signals produced by second two types of the nucleotide triphosphates in the mixture, thereby acquiring a first signal pattern; (d) repeating steps (b) and (c) using the polymerase, the template nucleic acid, and a second mixture of nucleotide triphosphates, wherein one of the first two types of the nucleotide triphosphates is in a distinguishable state compared to the other of the first two types of the nucleotide triphosphates in the second mixture, thereby acquiring a second signal pattern; and (e) comparing the first and second signal patterns to determine the sequence of the template nucleic acid.

BRIEF DESCRIPTION OF THE DRAWINGS

FIG. 7A and FIG. 7B show a combination of parameters that can be used to uniquely identify four different nucleotide types incorporated into a nucleic acid during a sequencing reaction using a polymerase attached to a SWNT FET. As shown, modified nucleotides that combine polarity-inverting and kinetic modifications can encode four different bases.

FIG. 8A and FIG. 8B shows a sequencing scheme where at any time a polymerase is in contact with a mixture of three natural and one modified dNTPs. Alignment of current traces for the four different runs allows the unique identification of all four bases of DNA.

FIG. 9A and FIG. 9B shows a sequencing scheme where at any time a polymerase is in contact with a mixture of two natural and two modified dNTPs. Alignment of the current traces for the two different runs allows the unique identification of four bases of DNA.

DETAILED DESCRIPTION

Figure 1:
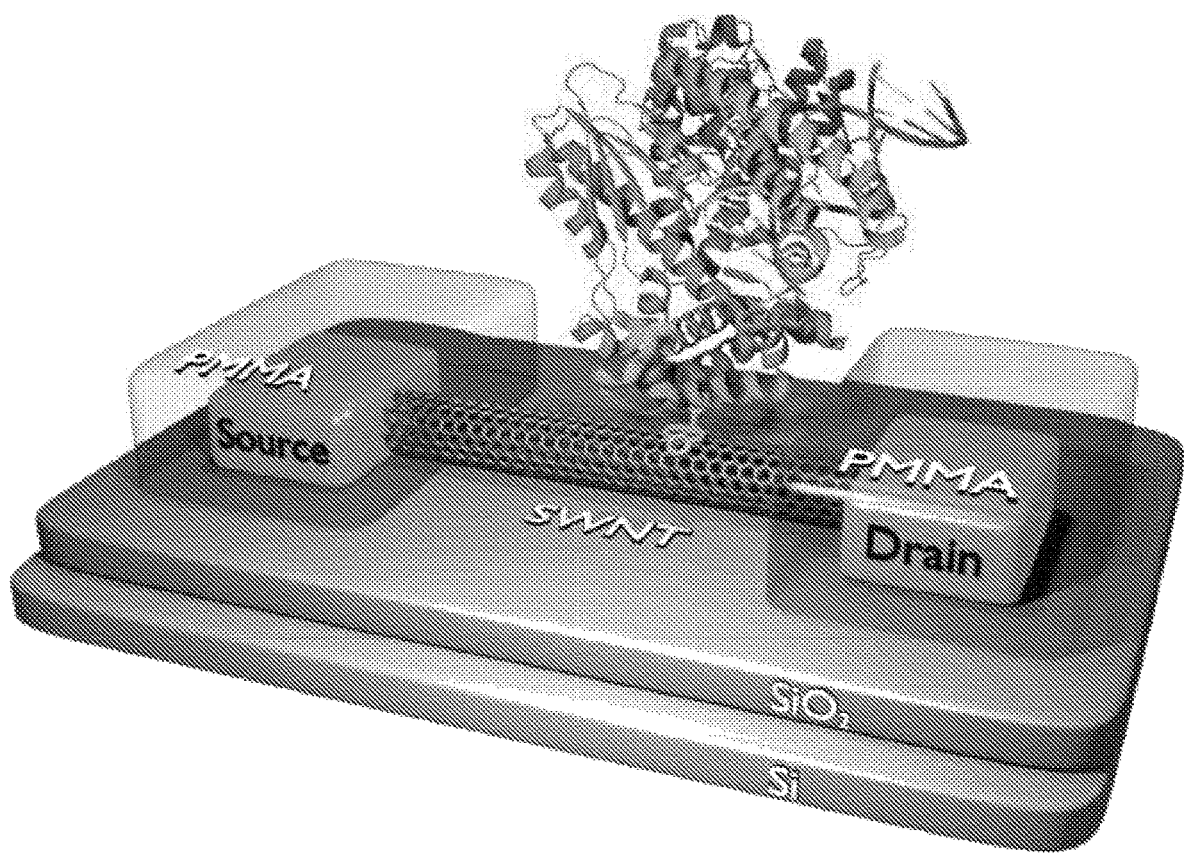
FIG. 1 shows a single enzyme immobilized on a SWNT FET

Embodiments of the present disclosure relate generally to apparatus, compositions and methods useful for single molecule detection in applications such as nucleotide incorporation events detected in nucleic acid sequencing procedures. There is a need for improved detection systems which provide long sequencing reads in high-throughput manner. Embodiments of the invention set forth herein satisfy this need and provide other advantages as well.

The present disclosure provides a method for sequencing nucleic acids. The method utilizes polymerase catalyzed incorporation of nucleotides into a nascent nucleic acid strand against a nucleic acid template. The polymerase can be attached to a charge sensor that detects nucleotide incorporation events. One or more non-natural nucleotide types that each produce a unique signatures at the charge sensor can be used to uniquely identify different nucleotides in the template nucleic acid.

In some embodiments, one or more non-natural nucleotide that are present in a mixture will produce a signal change having an inverted polarity compared to other nucleotides in the mixture. Alternatively or additionally, one or more non-natural nucleotide that is used in the mixture will produce a delay in nucleotide incorporation or reduced rate of incorporation. Alternatively or additionally, one or more non-natural nucleotide that is used in the method will produce a significantly altered signal height. These signal parameters can be detected in order to distinguish the nucleotides in a template nucleic acid to which the non-natural nucleotides complement during polymerase activity.

In particular embodiments, a non-natural moiety or modification that is present in the non-natural nucleotide(s) can produce a change in polymerase conformation (compared to the conformation produced by a nucleotide that lacks the moiety or modification) thereby producing a unique signature in one or more signal parameter detected by a charge sensor to which the polymerase is attached. Exemplary signal parameters include, but are not limited to, signal duration, signal height, signal rise time, signal fall time, signal polarity, signal noise, and the like.

Some embodiments of the method utilize a mixture of four different types of nucleotide triphosphates in which one of the nucleotide triphosphate types is present in a substantially lower amount or concentration (i.e. the low' nucleotide) compared to the other three types (i.e. the 'high' nucleotides). As a result, incorporation of the low nucleotide will be detectable as a relative delay or decreased incorporation rate. This signature can be exploited to identify the location in the template of the nucleotide type that complements the low nucleotide. Several sequencing runs can be completed for the same template, wherein each run is carried out with a different nucleotide in the low' state. The signal patterns from the different runs can be compared to determine the sequence of the template.

The above embodiment is exemplified in terms of a 3 'high'-1 'low' mixture of nucleotide triphosphates. It is possible to use other mixtures as well including, for example, a 1 'high'-3 'low' mixture, or a 2 'high'-2 'low' mixture. Further useful configurations of mixtures with regard to using nucleotides having different concentrations are set forth in U.S. Pat. No. 7,556,922, which is incorporated herein by reference.

In particular embodiments the template nucleic acid is circular. The use of a circular template can provide a convenient format for repeated sequencing runs since the polymerase need not be replaced and can instead make multiple laps around the template, each lap being effectively a repeated sequencing of the template.

In some embodiments that utilize a circular template, the polymerase can include a 5' exonuclease activity to digest a nucleic acid strand that is to be displaced from the circular template when the polymerase proceeds multiple times around the template.

Whether the template is linear or circular, a different primer can be used for different sequencing runs carried out on the same template. The different primers can be designed to hybridize at different locations on the template. As such, each of the runs will start at a different location in the template, but there can be substantial overlap between the portions of the template that are sequenced in each run. The signal patterns resulting from each run can be aligned based on the expected start sites for each run in order to facilitate sequence calling and error checking.

A charge sensor that is used in a method set forth herein can detect nucleotide incorporation by polymerase via a field effect using a SWNT FET, nanowire FET, FinFET, trigate FET, tunneling FET, or another field sensitive device. In some embodiments, the sensor is magnetic, electrochemical, or nanoelectromechanical.

Terms used herein will be understood to take on their ordinary meaning unless specified otherwise. Examples of several terms used herein and their definitions are set forth below.

As used herein, the term "array" refers to a population of charge sensors or molecules that are attached to one or more solid-phase substrates such that the charge sensors or molecules can be differentiated from each other according to their relative location. An array can include different molecules that are each located at a different addressable location (e.g. at different charge sensors) on a solid-phase substrate. Alternatively, an array can include separate solid-phase substrates each bearing a different molecule, wherein the different probe molecules can be identified according to the locations of the solid-phase substrates on a surface to which the solid-phase substrates are attached. The molecules of the array can be nucleic acid primers, nucleic acid probes, nucleic acid templates or nucleic acid enzymes such as polymerases.

As used herein, the term "attached" refers to the state of two things being joined, fastened, adhered, connected or bound to each other. For example, a reaction component, such as a polymerase, can be attached to a solid phase component, such as a charge sensor, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "charge sensor" is intended to mean a detection device that translates perturbations at its surface or in its surrounding electrical field into an electrical signal. For example, a charge sensor can translate the arrival or departure of a reaction component into an electrical signal. A charge sensor can also translate interactions between two reaction components, or conformational changes in a single reaction component, into an electrical signal. An exemplary charge sensor is a field effect transistor (FET) such as a single-walled carbon nanotube (SWNT) based FET, silicon nanowire (SiNW) FET, graphene nanoribbon FET (and related nanoribbon FETs fabricated from 2D materials such as $MoS_2$, silicene, etc), tunnel FET (TFET), and steep subthreshold slope devices (see, for example, Swaminathan et al., *Proceedings of the 51st Annual Design Automation Conference on Design Automation Conference*, pg 1-6, ISBN: 978-1-4503-2730-5 (2014) and Ionescu et al., *Nature* 479, 329-337 (2011)). Examples of FET and SWNT sensors that can be used in the methods and apparatus of the present disclosure are set forth in US Pat. App. Pub. No. 2013/0078622 A1, which is incorporated herein by reference.

As used herein, the term "conformational signal change" means the appearance, disappearance, or alteration of a detectable signal from a molecule in response to a change in the structure, shape or arrangement of parts of the molecule. For example, the signal change can be due to a change in the interaction of a label with a first portion of the molecule to interact with a second portion of the molecule.

As used herein, the term "conformationally labeled," when used in reference to a molecule, means having at least one label that is responsive to a change in the structure of the molecule, a change in the shape of the molecule or a change in the arrangement of parts of the molecule. The molecule can be, for example, a polymerase, reverse transcriptase, exonuclease or other nucleic acid enzyme. The parts of the molecule can be, for example, atoms that change relative location due to rotation about one or more chemical bonds occurring in the molecular structure between the atoms. The parts of the molecule can be domains of a macromolecule such as those commonly known in the relevant art. For example, polymerases include domains referred to as the finger, palm and thumb domains. In the case of proteins the parts can be regions of secondary, tertiary or quaternary structure. The label(s) can be attached to the molecule, for example, via a covalent linkage. However, the label(s) need not be attached to the molecule, being, for example, located in proximity to the molecule. In particular embodiments, the label is not attached to a reactant or product of the molecule such as a nucleotide or nucleic acid.

As used herein, the term "different", when used in reference to nucleic acids, means that the nucleic acids have nucleotide sequences that are not the same as each other. Two or more different nucleic acids can have nucleotide sequences that are different along their entire length. Alternatively, two or more different nucleic acids can have nucleotide sequences that are different along a substantial portion of their length. For example, two or more different nucleic acids can have target nucleotide sequence portions that are different for the two or more molecules while also having a universal sequence portion that is the same on the two or more molecules. The term "different" can be similarly applied to other molecules, such as polymerases and nucleic acid enzymes.

As used herein, the term "distinguishable state," when used in reference to a particular type of nucleotide triphosphate in a mixture of nucleotide triphosphates, is intended to mean the particular type of nucleotide triphosphate has a characteristic or property that manifests uniquely under a detection condition compared to other nucleotide triphosphates. Exemplary distinguishable states include, but are not limited to, being present in a quantity or concentration that is substantially less than the quantity or concentration of the other types of nucleotide triphosphates in the mixture, being present in a quantity or concentration that is substantially greater than the quantity or concentration of the other types of nucleotide triphosphates in the mixture, having a chemical moiety or modification that is not present on other types of nucleotide triphosphates in the mixture, or lacking a chemical moiety or modification that is present on other types of nucleotide triphosphates in the mixture. The distinguishable state can manifest when the nucleotide type interacts with a polymerase.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "label," when used in reference to a reaction component, is intended to mean a detectable reaction component or detectable moiety of a reaction component. A useful label is a charge label that can be detected by a charge sensor. A label can be intrinsic to a reaction component that is to be detected (e.g. a charged amino acid of a polymerase) or the label can be extrinsic to the reaction component (e.g. a non-naturally occurring modification of an amino acid).

As used herein, the term "non-natural," when used in reference to a moiety of a molecule, is intended to refer to a moiety that is not found attached to the molecule in its natural milieu or in a biological system unperturbed by human, technical intervention. Typically, non-natural moieties are synthetic modifications of molecules that render the molecules structurally or chemically distinct from the unmodified molecule or from molecules having natural modifications. As used herein, the term "non-natural," when used in reference to an analog used for a process, is intended to mean an analog that is not found in the natural milieu where the process occurs. Typically, non-natural analogs are synthetic analogs that are structurally or chemically distinct from other types of molecules in the class to which the analog belongs. It will be understood, that a molecule can be non-natural due to absence of a moiety that is found in the natural analog of the molecule.

As used herein, the term "nucleic acid" is intended to be consistent with its use in the art and includes naturally occurring nucleic acids or functional analogs thereof. Particularly useful functional analogs are capable of hybridizing to a nucleic acid in a sequence-specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art such as peptide nucleic acid (PNA) or locked nucleic acid (LNA). Naturally occurring nucleic acids generally have a deoxyribose sugar (e.g. found in deoxyribonucleic acid (DNA)) or a ribose sugar (e.g. found in ribonucleic acid (RNA)).

A nucleic acid can contain any of a variety of analog sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid are known in the art.

As used herein, the term "nucleotide" is intended to include natural nucleotides, analogs thereof, ribonucleotides, deoxyribonucleotides, dideoxyribonucleotides and other molecules known as nucleotides. The term can be used to refer to a monomeric unit that is present in a polymer, for example to identify a subunit present in a DNA or RNA strand. The term can also be used to refer to a molecule that is not necessarily present in a polymer, for example, a molecule that is capable of being incorporated into a polynucleotide in a template dependent manner by a polymerase. The term can refer to a nucleoside unit having, for example, 0, 1, 2, 3 or more phosphates on the 5' carbon. For example, tetraphosphate nucleotides and pentaphosphate nucleotides can be particularly useful. Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides include those that are not present in a natural biological system or not substantially incorporated into polynucleotides by a polymerase in its natural milieu, for example, in a non-recombinant cell that expresses the polymerase. Particularly useful non-natural nucleotides include those that are incorporated into a polynucleotide strand by a polymerase at a rate that is substantially faster or slower than the rate at which another nucleotide, such as a natural nucleotide that base-pairs with the same Watson-Crick complementary base, is incorporated into the strand by the polymerase. For example, a non-natural nucleotide may be incorporated at a rate that is at least 2 fold different, 5 fold different, 10 fold different, 25 fold different, 50 fold different, 100 fold different, 1000 fold different, 10000 fold different or more when compared to the incorporation rate of a natural nucleotide. A non-natural nucleotide can be capable of being further extended after being incorporated into a polynucleotide. Examples include, nucleotide analogs having a 3' hydroxyl or nucleotide analogs having a reversible terminator moiety at the 3' position that can be removed to allow further extension of a polynucleotide that has incorporated the nucleotide analog. Examples of reversible terminator moieties that can be used are described, for example, in U.S. Pat. Nos. 7,427,673; 7,414,116; and 7,057,026 and PCT publications WO 91/06678 and WO 07/123744, each of which is incorporated herein by reference. It will be understood that in some embodiments a nucleotide analog having a 3' terminator moiety or lacking a 3' hydroxyl (such as a dideoxynucleotide analog) can be used under conditions where the polynucleotide that has incorporated the nucleotide analog is not further extended. In some embodiments, the nucleotide(s) will not include a reversible terminator moiety, or the nucleotides(s) will not include a non-reversible terminator moiety or the nucleotide(s) will not include any terminator moiety at all. Nucleotide analogs with modifications at the 5' position are also useful.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments are located within a flow cell apparatus.

As used herein, the term "type" (or "species") is used to identify molecules that share the same chemical structure. For example, a mixture of nucleotides can include several dCTP molecules. The dCTP molecules will be understood to be the same type or species as each other. Similarly, individual DNA molecules that have the same sequence of nucleotides are the same type or species.

The embodiments set forth below and recited in the claims can be understood in view of the above definitions.

The methods and apparatus set forth herein can provide long nucleic acid sequencing reads; fast reads; high throughput capability for sequencing; and a scalable platform for sequencing. In some embodiments, any compromises in single read accuracy can be mitigated by performing multiple overlapping reads due to the ability of the methods and apparatus set forth herein to provide throughput in the number of reads performed in parallel.

The present disclosure provides a method of nucleic acid sequencing. The method can include steps of (a) providing a polymerase attached to a solid support charge sensor; (b) contacting the polymerase with a mixture of nucleotide triphosphates, wherein the mixture includes different types of nucleotide triphosphates, wherein a first type of the nucleotide triphosphates is in a distinguishable state compared to the other types of nucleotide triphosphates in the mixture, wherein a second type of the nucleotide triphosphates is not in the distinguishable state compared to the other types of nucleotide triphosphates in the mixture, and wherein the polymerase incorporates nucleotides from the mixture into a nascent strand against a template nucleic acid strand; (c) detecting the incorporation of the nucleotides via the charge sensor, wherein the first type of the nucleotide triphosphates produces a signal that is unique compared to signals produced by other nucleotide triphosphates in the mixture, thereby acquiring a first signal pattern; (d) repeating steps (b) and (c) using the polymerase, the template nucleic acid, and a second mixture of nucleotide triphosphates, wherein the second type of the nucleotide triphosphates is in a distinguishable state compared to the other types of nucleotide triphosphates in the second mixture, and wherein the first type of the nucleotide triphosphates is not in the distinguishable state compared to the other types of nucleotide triphosphates in the second mixture, thereby acquiring a second signal pattern; and (e) comparing the first and second signal patterns to determine the sequence of the template nucleic acid.

An exemplary sensor is shown in FIG. 1. Here a polymerase creates a reaction site where nucleotides can be incorporated into a primed DNA template. The polymerase is attached to a charge sensor (e.g. a single-walled carbon nanotube (SWNT)). The apparatus provides single molecule sensitivity. Changes in charge distribution at the reaction site (e.g. polymerase conformation changes, nucleotide incorporation, arrival or departure of charged tags etc.) transmit to the gate and can be detected.

Figure 2:
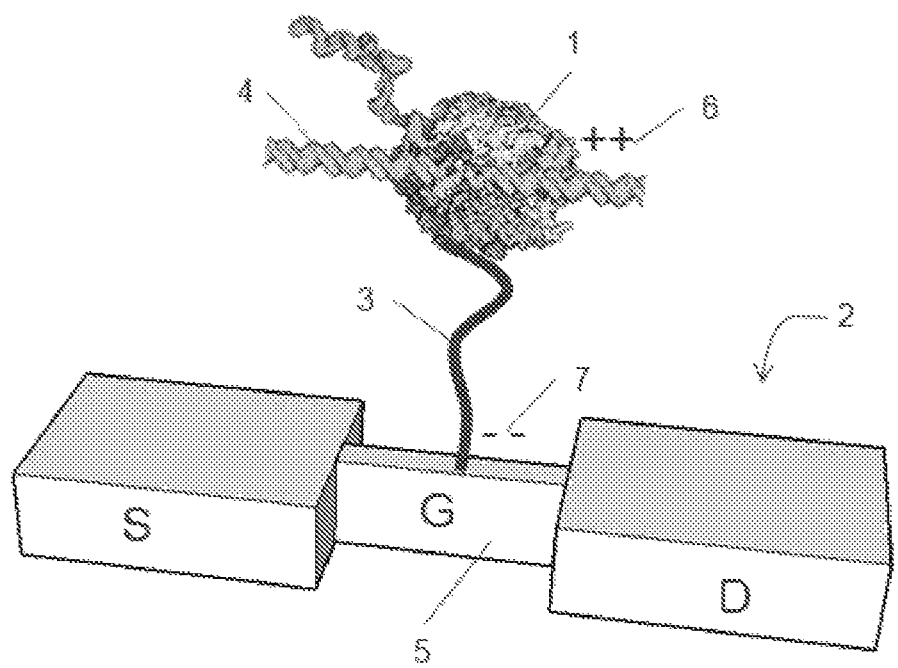
FIG. 2 shows a polymerase attached to a charge sensor via a tether.

An alternative to the configuration shown in FIG. 1 is to attach the polymerase to a charge sensor via a tether. An exemplary embodiment is shown in FIG. 2. Briefly, polymerase 1 is immobilized on the gate 5 of a silicon nanowire field-effect transistor (FET) 2 with a tether 3. Optionally, the tether 3 can be a conductive polymer strand, as indicated by the positive charge 6 at the end of the tether that is proximal to the polymerase and the negative charge 7 at the end of the tether that is distal to the polymerase and attached to the gate 5. The ssDNA 4 to be sequenced is bound to polymerase 1 after having been introduced in solution along with nucleotides and other reactants. As the complementary strand is synthesized, disturbances in the charge distribution in the vicinity of the FET 2 are generated, either as a result of conformational changes of the polymerase 1, or due to presence of the nucleotides. Those modifications in the charge distribution are sensed by the nanowire-FET 2 and detected as a modulation in the FET transconductance current.

Although the above examples describe SWNT and FET charge sensors, any of a variety of charge sensors can be used. Useful charge sensors include analytical devices that can incorporate a reaction component in direct spatial contact with a transduction element in a way to allow the rapid and convenient conversion of reaction events to detectable signals. Devices based on field-effect transistors (FETs) can directly translate interactions between reaction components (e.g., polymerases) and the transistor surface into readable electrical signals. In a standard FET, current flows along a conducting path (the channel) that is connected to two electrodes, (the source and the drain). The channel conductance between the source and the drain is switched on and off by a third (gate) electrode that can be capacitively coupled through a thin dielectric layer.

In particular embodiments, FETs are configured to accomplish single molecule detection. More particularly, these charge sensors can be configured to monitor the dynamics of a single molecule reaction. Any type of conduction channel that is generally found in field effect transistors can be used in an apparatus or method set forth herein. Exemplary conduction channels are formed from metals, metal oxides, semiconductors, or nanometer-scale conductors such as nanowires, or graphene.

Particularly useful charge sensors for single molecule detection are single-walled carbon nanotubes (SWNTs). See, for example, Star et al., *Nano. Lett.* 3, 459 (2003); Star et al., *Org. Lett.* 6, 2089 (2004); Besterman et al., *Nano. Lett.* 3, 727 (2003); Gruner, *Anal. Biooanal. Chem.* 384, 322 (2005); Chen et al. *Proc. Natl. Acad. Sci. U.S.A.* 100, 4984 (2003) and US Pat App. Pub. No. 2013/0078622 A1, each of which is incorporated herein by reference. SWNTs are extremely small conductors, typically on the order of about 1 nanometer in diameter.

A SWNT can be coated with a chemoselective polymer, metal or metal oxide nanoparticle, or reaction components like proteins, nucleic acids or antibodies. See for example, Besterman et al., *Nano. Lett.* 3, 727 (2003); and Chen et al. *Proc. Natl. Acad. Sci. U.S.A.* 100, 4984 (2003). Single polymerases can be attached to these SWNT and other charge sensors using methods set forth herein.

In some embodiments a single polymerase can be attached to a charge sensor by creating one single covalent defect on the charge sensor, for example, using techniques set forth in Goldsmith et al. *Science* 315, 77 (2007), which is incorporated herein by reference. For example a SWNT can be produced having a single defect such that a variety of attachment chemistries can be used to link a single polymerase to the reactive defect site selectively, without coating the rest of the SWNT with additional polymerases. SWNTs can also be attached to polymerase by non-covalent means, for example, using techniques set forth in Chen et al, *J. Am. Chem. Soc.* 123, 3838 (2001), which is incorporated herein by reference. These methods can be modified as set forth herein to reliably bind a single polymerase non-covalently to a SWNT.

SWNTs are semiconductors with electron bandgaps that can vary from 1 electron volt to effectively zero. SWNTs are useful as conduction channels because single molecule sensing devices can be fabricated from SWNT wires of any type, with or without gate electrodes, and on glass, plastic, or silicon substrates. Useful SWNTs and their configurations for single molecule detection are set forth in US Pat App. Pub. No. 2013/0078622 A1, which is incorporated herein by reference.

Other charge sensors that can be modified for use in an apparatus or method set forth herein include, without limitation, silicon nanowire (SiNW) FET, FET made of III-V materials, silicon FinFET, graphene nanoribbon FETs as well as nanoribbon FETs from other 2D materials such as $MoS_2$ and silicene, tunnel FET (TFET), and steep subthreshold slope devices (see, for example, Swaminathan et al., *Proceedings of the 51st Annual Design Automation Conference on Design Automation Conference*, pg 1-6, ISBN: 978-1-4503-2730-5 (2014) and Ionescu et al., *Nature* 479, 329-337 (2011)).

In particular embodiments, an apparatus or method of the present disclosure uses deeply scaled FinFET transistors as single-molecule charge sensors. FinFet sensors benefit from technology already under development by leading edge semiconductor manufacturers. Furthermore, previously published components can be used, including but not limited to (1) those used for immobilization of lysozyme on CNT to observe enzyme processivity in real time as described in Choi et al, *Science*, 335, 319 (2012), (2) those used to immobilize the Pol 1 Klenow fragment on CNT and observe DNA processivity in real time as described in Olsen et al, *J. Amer. Chem. Soc.*, 135, 7885 (2013), (3) those used to elucidate a transduction mechanism as moving charged residues due to protein allosteric motion as described in Chi et al, *NanoLett* 13, 625 (2013). The present methods can also employ the apparatus and methods set forth in US Pat. App. Pub. No. 2013/0078622 A1. Each of the above references is incorporated herein by reference.

Figure 3:
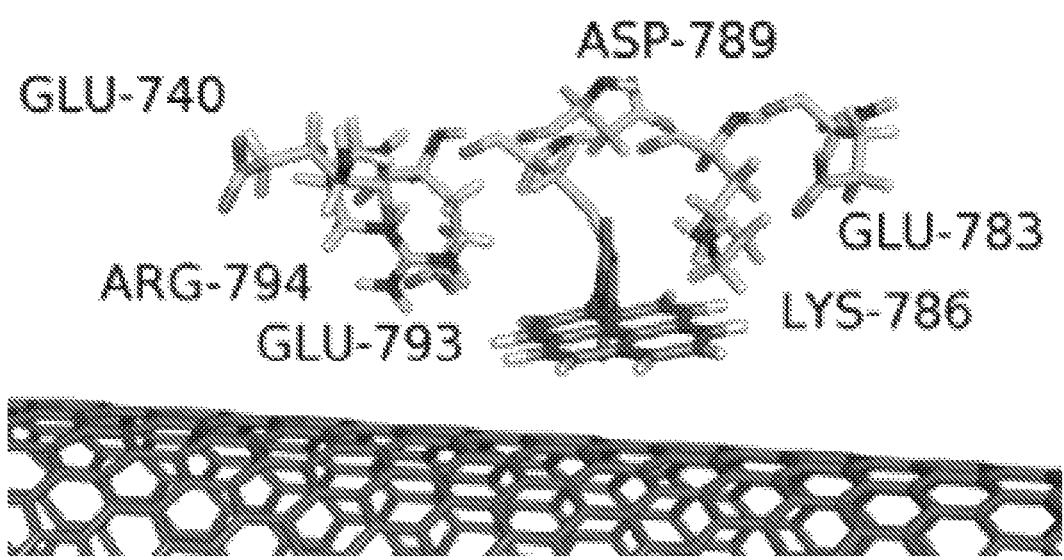
FIG. 3 shows charged residues for the Klenow fragment of DNA Polymerase I in the vicinity of a nanowire charge sensor.

Although not intending to be limited by theory, it is believed that the motion of charged residues on a polymerase that is in the vicinity of a charge sensor will create external electric fields that are sensed by the charge sensor. For example, charged residues for the Klenow fragment of DNA Polymerase I that are believed to cause field effects when in the vicinity of the attachment point of a polymerase to a SWNT FET are shown in FIG. 3.

Figure 4A:
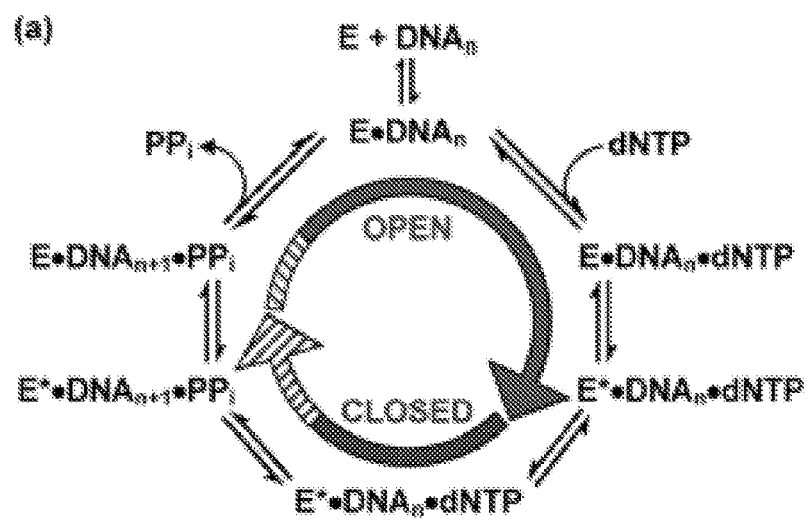
FIG. 4A shows a catalytic cycle of polymerase activity.
Figure 4B:
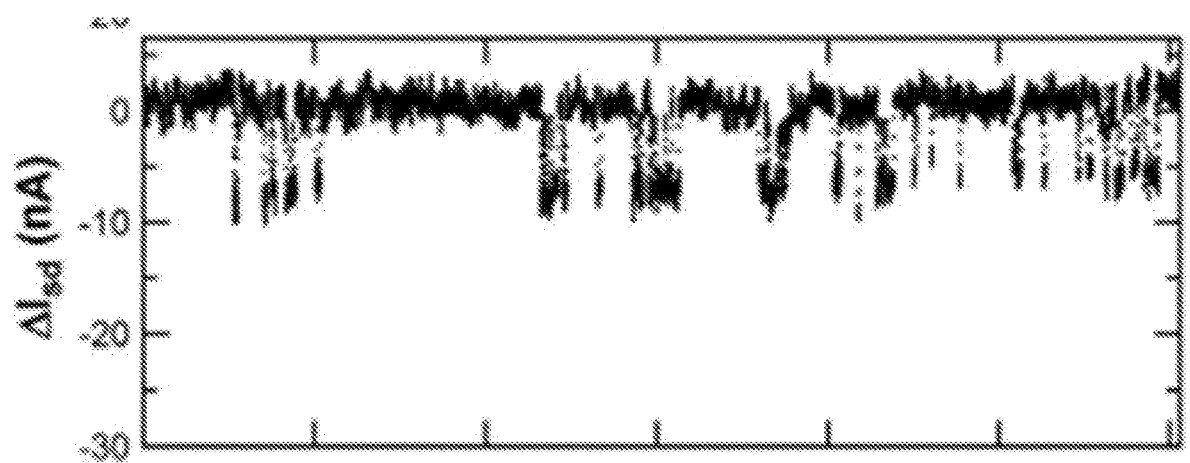
FIG. 4B shows exemplary signals detected by a polymerase attached to a SWNT FET during nucleotide incorporation into a primed template nucleic acid.

FIG. 4A shows a diagram of a catalytic cycle for polymerase activity. As the polymerase goes through its catalytic cycle, the changes in conformation (e.g. at the residues shown in FIG. 3 or other residues) can result in a time-dependent transient signal as each nucleotide is incorporated. An exemplary signal pattern detected by a polymerase attached to a SWNT FET during nucleotide incorporation into a primed template nucleic acid is shown in FIG. 4B.

In some embodiments, the signal from electronic monitoring of conformation changes is not capable of base discrimination, for example, when duration and intensity of the current modulations detected by the charge sensor cannot be differentiated on the basis of the type of nucleotide that is added in each polymerase cycle. In such embodiments, the number of bases that is added by a polymerase against a template strand can be detected. It is also possible to flow in a single nucleotide type at a time and to correlate detection of nucleotide addition with the type of nucleotide known to be in contact with the polymerase. However, in other embodiments it is desired to achieve base discrimination for polymerases that are detected by charge sensors in the presence of several different nucleotide types. The advantages of using mixtures of different nucleotide types, as opposed to single nucleotide types, is more rapid and cost effective sequence analysis (e.g. due to reduced number of fluidic steps) and increased accuracy of sequencing (e.g. due to reduced occurrence of errors when polymerase has access to a more complete repertoire of nucleotide types).

Alternative embodiments, can be configured to distinguish different types of nucleotides based on detection of characteristic signal parameters. One such signal parameter is the polarity of signal changes detected when a particular type of nucleotide triphosphate is incorporated into a nascent nucleic acid. For example, a first nucleotide type can produce a positive change in signal polarity when incorporated by a polymerase into a nascent nucleic acid strand, and this can be distinguished from a negative change in signal polarity that is produced when the polymerase incorporates a second type of nucleotide into the nascent nucleic acid strand.

Nucleotide triphosphates can include non-natural moieties that impact the polarity of signal change observed when they are incorporated into a nascent nucleic acid strand by a charge sensor-attached polymerase. In particular embodiments, a non-natural moiety can produce an interaction with polymerase that is distinguishable from the interaction the polymerase has with other nucleotide triphosphates that lack the moiety. For example, the native nucleotides deoxyadenosine triphosphate (ATP), deoxythymidine triphosphate (dTTP), deoxycytosine triphosphate (dCTP) and deoxyguanosine triphosphate (dGTP) produce signals of the same polarity when interacting with a charge sensor-attached polymerase, as do several known nucleotide analogs. A mixture can be used where one or more of the native nucleotide triphosphates is replaced with an analog having a non-natural moiety that alters signal polarity in a distinguishable way without having an adverse impact on the ability of the analog to base pair with its cognate nucleotide in a template strand during sequencing. The cognate nucleotide type can be distinguished from other nucleotide types in the template based on the unique signal polarity that is detected when the nucleotide triphosphate analog is incorporated.

Figure 5:
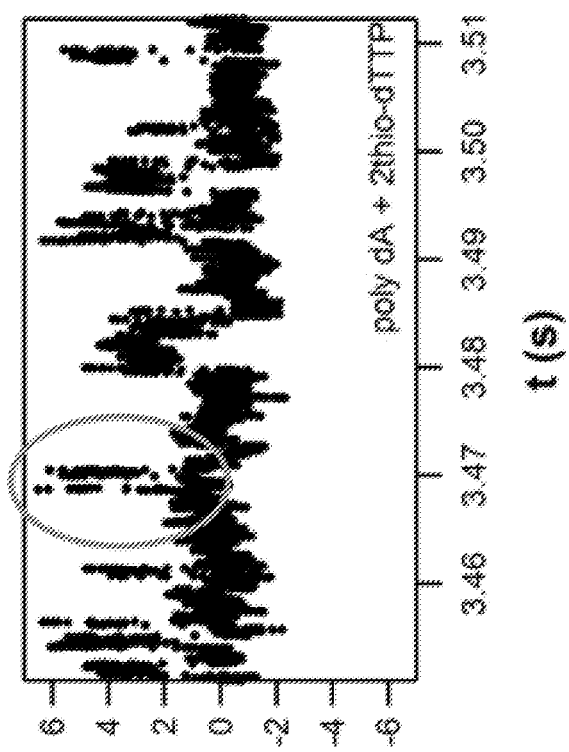
FIG. 5 shows exemplary signal detected by a polymerase attached to a SWNT FET during incorporation of natural and phosphate-modified dATP (left) and; during incorporation of 2-thio dTTP (right).
Figure 5:
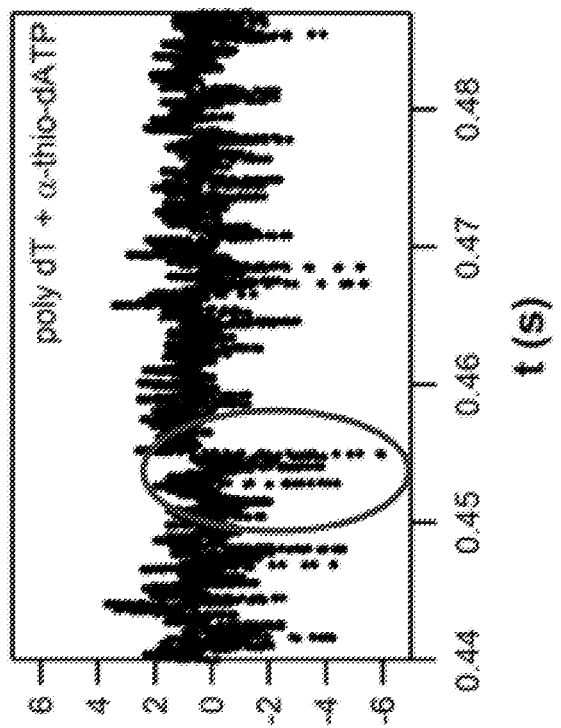

An example of two nucleotide triphosphate types that produce signals of opposite polarity is shown in FIG. 5. Specifically, alpha-thio-dATP can be incorporated into a nascent strand by charge sensor-attached polymerase using a polythymine template and the result is a negative change in signal polarity. In contrast, 2-thio-dTTP when incorporated by the same sensor-attached polymerase against a polyadenosine template will produce a positive change in signal polarity. As such, alpha-thio-dATP and 2-thio-dTTP can be used to distinguish T and A positions in a template using a charge sensor-attached polymerase as set forth herein. Other nucleotide triphosphate analogs that can be distinguished based on differences in polarity of signal changes can be used in a method set forth herein.

Another signal parameter that can differ based on the type of nucleotide triphosphate that is incorporated into a nascent nucleic acid strand by a sensor-attached polymerase, is the rate or time duration for the incorporation event. The rate or time duration of incorporation can be influenced by reaction conditions or the chemical structure of the nucleotide triphosphates used in the reaction. An example of a reaction condition that can be manipulated is the relative concentration of the nucleotide triphosphates used. A particular type of nucleotide triphosphate can be present in a relatively low amount or concentration which will result in a reduced rate of incorporation of that nucleotide type or a longer delay in its incorporation (compared to other nucleotide types). This difference will typically observed as a difference in average rate or average delay, but other measures such as a threshold value, minimum value or maximum value can be observed as well.

Figure 6A:
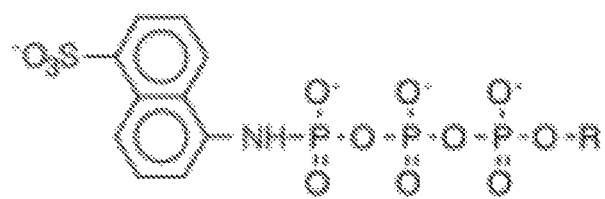
FIG. 6A shows chemical structure of γ-ANS nucleotide modification.
Figure 6B:
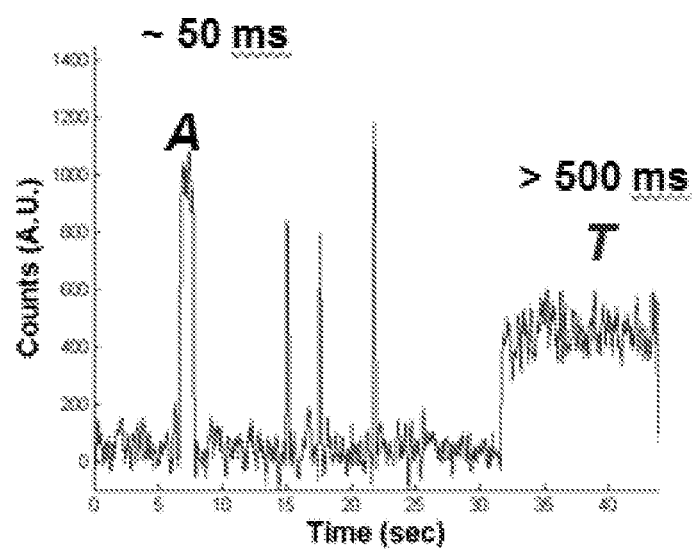
FIG. 6B shows FRET signal from a polymerase processing a mixture of natural (dATP) and γ-ANS modified nucleotides (dTTP). The duration of the closed state with γ-ANS dTTP is >10× longer than a natural nucleotide, allowing the identity of the base to be determined.

Nucleotide triphosphates can include non-natural moieties that impact the rate of incorporation or time duration for incorporation. FIG. 6A shows the chemical structure of γ-ANS nucleotide modification that can be incorporated at the 5' position of a nucleotide triphosphate to increase the duration of time that a polymerase spends in the closed state relative to the same nucleotide triphosphate that lacks the 5' modification. As shown in FIG. 6B, an optical signal detected for a polymerase in the presence of a mixture of natural dATP and γ-ANS modified dTTP, shows that the duration of the closed state with γ-ANS dTTP is over 10 times longer than observed with a natural nucleotide. See US Pat. App. Pub. No. 2011/0312529 A1 (which is incorporated herein by reference).

Methods that use time-based or kinetic discrimination of nucleotides, can be facilitated by use of very fast mixing of reagents at the charge sensors coupled with real time detection. The mixing can occur on the sub-milliseconds timescale in accordance with available stopped-flow instrumentation. The fast mixing of reagents can be achieved using fast fluidics, active or passive mixing, and proper confinement (e.g. mix blousing) of the reaction to overcome limitations by diffusion. Stopped-flow delivery is particularly useful. Stopped flow delivery provides delivery of fluid to a detection site using rapid flow of the fluid followed by abrupt stoppage of the flow. The fluid that is delivered typically displaces an equal volume of fluid from the detection site. The fluid can mix with a solid-phase analyte such as a polymerase attached to a charge sensor. The dead time for stopped-flow fluid delivery can be, for example, less than 2 milliseconds (msec). Accordingly, the dead time can be no longer than 2 msec, 1.5 msec, 1 msec, 0.8 msec, 0.6 msec, 0.5 msec or 0.4 msec. For useful stopped flow and rapid mixing fluidic systems see, for example, Chance, B. J. Frank. Inst., 229, 613 (1940), and US Pat. App. Pub. No. US 2013/0165328 A1, each of which is incorporated herein by reference.

A sequence of time-based or kinetic measurements for a charge-sensor attached polymerase can be used to determine the sequence of a template nucleic acid being used by the polymerase to synthesize a complementary strand. It will be understood that the sequence of the template strand can be inferred from the sequence of nucleotides incorporated into the strand that is being extended. As such, determination of the sequence of one strand will be understood to include determination of the sequence of its complementary strand.

Any of a variety of nucleotide species can be useful in a method or composition set forth herein. For example, naturally occurring nucleotides can be used such as ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Typically, dNTP nucleotides are incorporated into a DNA strand by DNA polymerases and NTP nucleotides are incorporated into an RNA strand by RNA polymerases. In particular embodiments, NTP nucleotides or analogs thereof can be incorporated into DNA by a DNA polymerase, for example, in cases where the NTP, or analog thereof, is capable of being incorporated into the DNA by the DNA polymerase and where the rate or time duration for a DNA polymerase transition using the NTP, or analog thereof, can be distinguished from the rate or time duration for the DNA polymerase transition using another nucleotide. Alternatively, dNTP nucleotides or analogs thereof can be incorporated into RNA by an RNA polymerase, for example, in cases where the dNTP, or analog thereof, is capable of being incorporated into the RNA by the RNA polymerase and where the rate or time duration for an RNA polymerase transition using the dNTP, or analog thereof, can be distinguished from the rate or time duration for the RNA polymerase transition using another nucleotide. Additionally, dNTP nucleotides or analogs thereof can be incorporated into DNA from an RNA template by a reverse transcriptase, for example, in cases where the dNTP, or analog thereof, is capable of being incorporated into the DNA from an RNA template by a reverse transcriptase and where the rate or time duration for a reverse transcriptase transition using the dNTP, or analog thereof, can be distinguished from the rate or time duration for the reverse transcriptase transition using another nucleotide. The relative difference in rate or time duration can be a relative increase in the rate, a relative increase in duration, a relative decrease in rate or a relative decrease in duration.

Non-natural nucleotide analogs are also useful. Particularly useful non-natural nucleotide analogs include, but are not limited to, those that produce a detectably different rate or time duration for a polymerase transition that can be distinguished from the rate or time duration for a polymerase transition with another nucleotide. For example, a non-natural nucleotide analog may usefully produce a detectably different rate or time duration for a polymerase transition that can be distinguished from the rate or time duration for the same transition of the polymerase with another nucleotide such as a naturally occurring nucleotide. Exemplary nucleotide analogs that can be used include, but are not limited to, dNTPαS; NTPαS; nucleotides having unnatural nucleobases identified in Hwang et al., *Nucl. Acids Res.* 34:2037-2045 (2006) (incorporated herein by reference) as ICS, 3MN, 7AI, BEN, DM5, TM, 2Br, 3Br, 4Br, 2CN, 3CN, 4CN, 2FB, 3FB, MM1, MM2 and MM3; or nucleotides having other non-natural nucleobases such as those described in Patro et al. *Biochem.* 48:180-189 (2009) (incorporated herein by reference) which include 2-amino-1-deazapurine, 1-deazapurine, 2-pyridine, hypoxanthine, purine, 6-Cl-purine, 2-amino-dA, 2-amino purine or 6-Cl-2-amino-purine or nucleotides having non-natural nucleobases such as those described in Krueger et al. *Chem Biol.* 16:242-8 (2009) (incorporated herein by reference) which include iso-G, iso-C, 5SICS, MMO2, Ds, Pa, FI, FB, dZ, DNB, thymine isosteres, 5-NI, dP, azole-carboxamide, xA, Im-No, Im-ON, J, A*, T*.

Non-natural nucleotide analogs having 5' modifications are particularly useful. The non-natural nucleotide analog will typically have a triphosphate but can have more or fewer phosphates. In particular embodiments, one or more of the alpha phosphate, beta phosphate or gamma phosphate of a non-natural nucleotide is covalently attached to a moiety other than oxygen. A moiety that is attached to a phosphate or otherwise present at the 5' position can provide a negative charge, a positive charge, metal-chelating activity or steric bulk. Exemplary moieties include, but are not limited to, amino acids, in the L-enantiomer form or R-enantiomer form, such as histidine, aspartate, glutamate, tryptophan, phenylalanine, methionine, tyrosine, cysteine, glycine alanine, or proline; an amino group; a chelated metal such as magnesium or manganese; a methyl group; a halogen such as bromine, chlorine or iodine; a thiol group; an electron withdrawing group; an electron donating group; an aromatic amine; or an aliphatic amine. These and other moieties may be advantageous in embodiments where they provide an interaction with a polymerase, or other nucleic acid enzyme, that differs from the interaction that the enzyme has with a nucleotide lacking the moiety. As such, the presence and absence of the moiety on respective nucleotide species can be exploited to distinguish the nucleotide species in a sequencing method, for example, based on the rate, time duration and/or intensity for a conformational signal change in a nucleic acid enzyme acting on the nucleotide species.

A reaction composition or method can include one or more nucleotide species. For example, a reaction composition or method used for sequence analysis can include four different nucleotide species capable of forming Watson-Crick base pairs with four respective nucleotide species in a nucleic acid template being synthesized. Particular embodiments can include at least two different nucleotide species, at least three different nucleotide species, at least four different nucleotide species, or more. At least two of the nucleotide species can be non-natural nucleotide analogs, at least three of the nucleotide species can be non-natural nucleotide analogs, or at least four of the nucleotide species can be non-natural nucleotide analogs. Thus a reaction composition or method can include a mixture of natural nucleotides and non-natural nucleotide analogs. Alternatively, a reaction composition can lack natural nucleotides having instead only non-natural nucleotide analogs. The reaction can be carried out under conditions in which only non-natural nucleotide analogs are incorporated into a growing nucleic acid by a polymerase.

In some embodiments, a reaction composition or method can include nucleotide species that base-pair with no more than one nucleotide species in a nucleic acid template. For example, a method can be carried out under conditions wherein different nucleotide species are contacted with a polymerase and nucleic acid in separate, sequential reactions. Specifically, a nucleotide species that base-pairs with A can be added in a first reaction, a nucleotide species that base-pairs with C can be added in a second reaction, a nucleotide species that base-pairs with T can be added in a third reaction, and a nucleotide species that base-pairs with G can be added in a fourth reaction. The reactions are referred to as first, second, third and fourth merely to illustrate that the reactions are separate but this does not necessarily limit the order by which the species can be added in a method set forth herein. Rather, nucleotide species that base-pair with A, C, T or G can be added in any order desired or appropriate for a particular embodiment of the methods. Typically in a sequencing method nucleotide species that base-pair with four different nucleotide species in a given template nucleic acid are added sequentially to complete a cycle of the sequencing method. However, it will be understood that fewer than four nucleotide additions can be used in some embodiments. Furthermore, it will be understood that mixtures of nucleotides that base-pair with more than one but no more than 2, 3 or 4 nucleotide species can be used. Similarly, mixtures of nucleotides that base-pair with more than two but no more than 3 or 4 nucleotide species can be used, or mixtures of nucleotides that base-pair with more than three but no more than 4 nucleotide species can be used.

The present disclosure provides a method of nucleic acid sequencing that includes steps of (a) providing a polymerase attached to a solid support charge sensor; (b) contacting the polymerase with a mixture of nucleotide triphosphates, wherein the mixture includes different types of nucleotide triphosphates, wherein a first two types of the nucleotide triphosphates are in a first distinguishable state compared to a second two types of the nucleotide triphosphates in the mixture, and wherein the polymerase incorporates nucleotides from the mixture into a nascent strand against a template nucleic acid strand; (c) detecting the incorporation of the nucleotides via the charge sensor, wherein the first two types of the nucleotide triphosphates produce a signal that distinguished from signals produced by second two types of the nucleotide triphosphates in the mixture, thereby acquiring a first signal pattern; (d) repeating steps (b) and (c) using the polymerase, the template nucleic acid, and a second mixture of nucleotide triphosphates, wherein one of the first two types of the nucleotide triphosphates is in a distinguishable state compared to the other of the first two types of the nucleotide triphosphates in the second mixture, thereby acquiring a second signal pattern; and (e) comparing the first and second signal patterns to determine the sequence of the template nucleic acid.

Some embodiments can employ a combination of the above-described signal parameters to distinguish multiple types of bases in a nucleic acid that is being sequenced. Differences in one or more parameters can be exploited to distinguish at least two, three or four different nucleotide types. Depending upon the parameter(s) used, a particular embodiment may distinguish at most two or three different nucleotide types.

An example of a combinatorial use of different parameters can be understood in view of the matrix shown in FIG. 7A and truth table shown in FIG. 7B. In this case four different nucleotide types are distinguished across several sequencing runs carried out for the same template and based on a combination of two different states in signal polarity change and two different states in nucleotide incorporation kinetics. Combinatorial methods can be used to identify a number of different nucleotide types in a nucleic acid that exceeds the number of different labels distinguished in a sequencing run. Exemplary combinations of states and stages that can be used for sequencing are set forth in US Pat. App. Pub. No. 2013/0079232 A1, which is incorporated herein by reference.

Particular embodiments employ a strategy of resequencing the same nucleic acid multiple times, but each time using a different mixture of nucleotide triphosphates. For example, a charge sensor-attached polymerase can be used to sequence a nucleic acid molecule using a dNTP mixtures containing three natural dNTPs and one non-natural dNTP analog that produces a unique signature in the current trace compared to the natural dNTPs. As shown in the matrix of FIG. 8A and truth table of FIG. 8B, a first run can use natural dATP, dTTP and dGTP along with a non-natural analog of dCTP that produces a unique signature; a second run can use natural dCTP, dTTP and dGTP along with a non-natural analog of dATP that produces a unique signature, etc. Aligning the current patterns from the four different runs allows the determination of the nucleotide sequence in the template strand via pattern recognition, removing the need to do individual base calls.

Although the combinatorial method of FIG. 8 is exemplified with regard to the use of 3 natural nucleotides and a single non-natural analog, it will be understood that different combinations of natural and/or non-natural nucleotide triphosphates can be used to achieve a similar result. For example, non-natural nucleotide triphosphates need not be used. Rather, four different non-natural analogs can be used.

Furthermore, although four different runs through the same nucleic acid stretch, each using one of four uniquely detectable nucleotide triphosphate analogs, can be used as exemplified in regard to FIG. 8, it is also possible to determine the locations of four different nucleotide types in a sequence using fewer than four runs. For example, an alternative strategy as shown in the matrix of FIG. 9A and truth table of FIG. 9B, uses only two different sequencing runs through the same stretch of nucleic acid. In this example, a first run produces two types of signals, a first signal type being degenerate with respect to G and C and a second signal type being degenerate with respect to T and A. However, a second run can be used to obtain a pattern of signals that when compared with the pattern from the first run will distinguish G from C and will distinguish T from A. Specifically, a first nucleotide type produces a particular signal that is the same in both runs (e.g. C in FIG. 9), a second nucleotide type produces that particular signal in the first run but not in the second run (e.g. G in FIG. 9), a third nucleotide type produces that particular signal in the second run but not in the first run (e.g. T in FIG. 9) and a fourth nucleotide type does not produce that particular signal in either run. Accordingly a comparison of both runs will unambiguously identify all four nucleotide types. In this example, the particular signal type can be produced for example, due to a non-natural moiety. As such the moiety can be present in the dGTP and dCTP, but absent from dATP and dTTP in the first run; and the moiety can be present in dTTP and dCTP, but absent from dGTP and dATP in the second run. Other conditions or chemical modifications that produce characteristic signal parameters, such as those exemplified elsewhere herein, can be differentially applied across runs to achieve a similar result.

It will be understood that unique signatures in the signal patterns can be derived from any of a variety signal parameters including, for example, polarity of current modulation; duration of a detectable state of a polymerase (e.g. duration of the open or closed state of the polymerase); amplitude of the current modulation; or any other signal characteristic which allows the unique identification of the modified nucleotide, for example noise, rise/fall time of the current pulse, or shape of the leading and/or trailing edge of the pulse.

Figure 10:
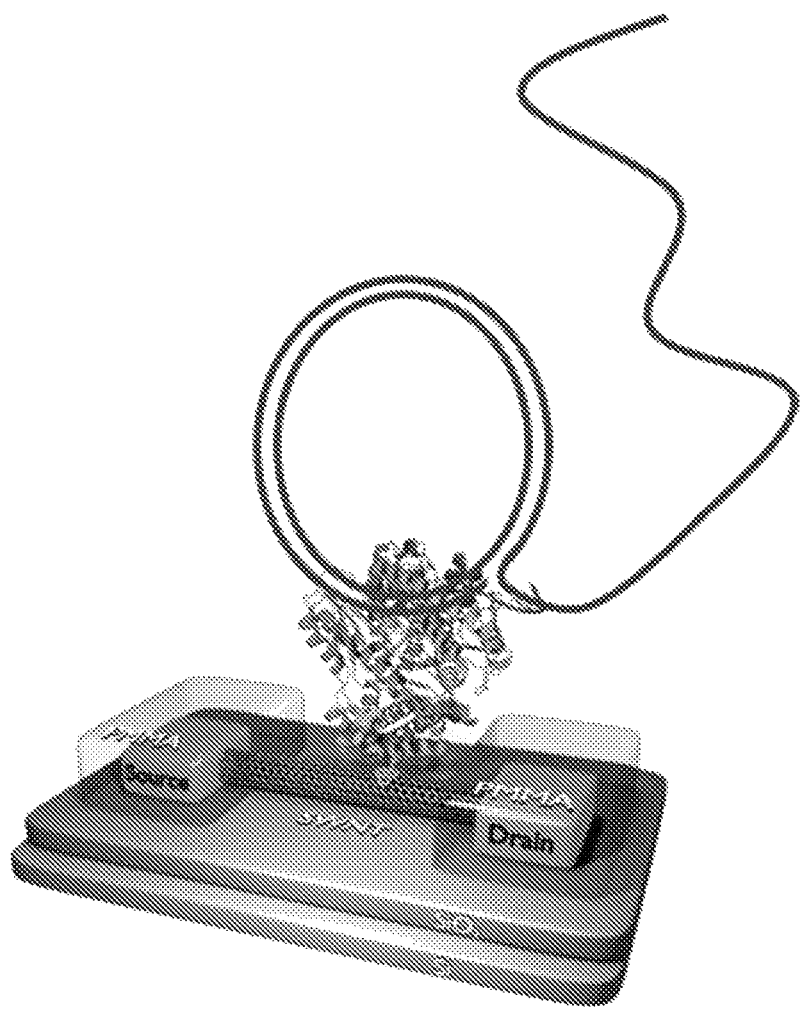
FIG. 10 shows a high-processivity polymerase configured to sequence a circular template as a means of increasing accuracy and aligning the current traces for "laps" around the template performed with dNTP mixtures having different analogs (e.g. different nucleotide modifications present during different laps).

In some embodiments, repeated sequencing can be achieved using a circular template with a high-processivity polymerase. See FIG. 10. This allows for consensus sequencing, where random errors are eliminated via increased sequencing depth. Another method is to use a sequencing primer that serves as a location marker for pattern alignment. Multiple runs can be performed with unique primers that hybridize at different locations in the template. The known locations of hybridization can be used when comparing multiple reads of the template. Such methods can be utilized to achieve genome scale coverage.

Although several embodiments have been exemplified herein with regard to SWNT FETs, it will be evident to those skilled in the art that any field-effect sensitive electronic device is in principle suitable for the detection of the motion of charged residues. For example Si nanowires (Yi Cui et al, *Nanolett, p.* 149, 2003), conducting polymer nanotubes (A. L. Briseno et al, *Mater. Today p.* 28, 2008), Fin-FETs and tri-gate FETs (X. Huang et al, *IEDM, p.* 67, 1999) and tunneling FETs (D. Sarkar, *Appl. Phys. Lett.* P. 143108, 2012) are all suitable sensors for this application. These references are incorporated herein by reference. Additionally, it will be appreciated that the proposed methods for base discrimination are extendible and applicable beyond field-effect sensors and are equally applicable to magnetic sensors, electrochemical sensors, tunneling sensors, and nano-electromechanical (NEMS) sensors.

The present disclosure provides multiplexed methods where several different nucleic acid molecules are sequence in parallel. A plurality of charge sensors can be provided in the form of an array of charge sensors. The array can include at least 10, 100, $1 \times 10^3$, $1 \times 10^4$, $1 \times 10^4$, $1 \times 10^4$ or more charge sensors. Each individual charge sensor can be located at a discrete location in the array that is separated from the other charge sensors in the array. For example, each charge sensor can reside in a well or depression in a solid support. The locations, even when separated from each other, can optionally be in fluid contact with a bulk solution. In such a configuration, multiplex reactions can occur on the array of charge sensors by delivering common reagents to all of the charge sensors via bulk fluid delivery. Taking nucleic acid sequencing reactions as an example, nucleotides can be delivered via bulk solution to an array of wells (or other features), each well (or other feature) hosting an individual sequencing reaction. The nucleotide delivery will result in parallel sequencing reactions at the wells (or other features).

A charge sensor, such as a nanowire can have dimensions that are less than 10 nm wide and greater than 100 nm long. A nanowire or other charge sensor can be placed in a well that is 10 nm×10 nm, 50 nm×100 nm or larger. For example, a well within which a charge sensor resides can have an opening on a surface that is at least 100 $nm^2$, 1000 $nm^2$, 5000 $nm^2$, $1 \times 10^4$ $nm^2$, or larger. The circuitry to read out the signal from the charge sensing element can occupy an area of the solid support that is 1 micron×1 micron or larger.

The density of an array can be from 2 to as many as a billion or more different reaction sites per square cm. Very high density arrays are useful in the invention including, for example, those having at least about 10,000,000 reaction sites/$cm^2$, including, for example, at least about 100,000,000 reaction sites/$cm^2$, 1,000,000,000 reaction sites/$cm^2$, up to about 2,000,000,000 reaction sites/$cm^2$ or higher. High density arrays can also be used including, for example, those in the range from about 100,000 reaction sites/$cm^2$ to about 10,000,000 reaction sites/$cm^2$. Moderate density arrays useful in the invention can range from about 10,000 reaction sites/$cm^2$ to about 100,000 reaction sites/$cm^2$. Low density arrays are generally less than about 10,000 reaction sites/$cm^2$.

Multiplex embodiments, including, for example, those that employ an array of charge sensors can be configured such that a single polymerase molecule is attached to each charge sensor. For example, the charge sensors in a multiplex embodiment can substantially all be attached to a single polymerase. Furthermore, the same species of polymerase can be attached to each of the charge sensor. This configuration can provide an expected uniform output from each charge sensor, but for differences in the other reaction components that come into contact with each respective charge sensor.

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases. Exemplary DNA polymerases include those that have been classified by structural homology into families identified as A, B, C, D, X, Y, and RT. DNA Polymerases in Family A include, for example, T7 DNA polymerase, eukaryotic mitochondrial DNA Polymerase γ, *E. coli* DNA Pol I, *Thermus aquaticus* Pol I, and *Bacillus stearothermophilus* Pol I. DNA Polymerases in Family B include, for example, eukaryotic DNA polymerases α, δ, and ε; DNA polymerase ζ; T4 DNA polymerase, Phi29 DNA polymerase, and RB69 bacteriophage DNA polymerase. Family C includes, for example, the *E. coli* DNA Polymerase III alpha subunit. Family D includes, for example, polymerases derived from the Euryarchaeota subdomain of Archaea. DNA Polymerases in Family X include, for example, eukaryotic polymerases Pol β, pol σ, Pol λ, and Pol μ, and *S. cerevisiae* Pol4. DNA Polymerases in Family Y include, for example, Pol η, Pol iota, Pol kappa, *E. coli* Pol IV (DINB) and *E. coli* Pol V (UmuD'2C). The RT (reverse transcriptase) family of DNA polymerases includes, for example, retrovirus reverse transcriptases and eukaryotic telomerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and Archaea RNA polymerase.

The above classifications are provided for illustrative purposes. It will be understood that variations in the classification system are possible. For example, in at least one classification system Family C polymerases have been categorized as a subcategory of Family X. Furthermore, polymerases can be classified according to other characteristics, whether functional or structural, that may or may not overlap with the structural characteristics exemplified above. Some exemplary characteristics are set forth in further detail below.

A polymerase having an intrinsic 3'-5' proofreading exonuclease activity can be useful for some embodiments. Polymerases that substantially lack 3'-5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

Polymerases can be characterized according to their processivity. A polymerase can have an average processivity that is at least about 50 nucleotides, 100 nucleotides, 1,000 nucleotides, 10,000 nucleotides, 100,000 nucleotides or more. Alternatively or additionally, the average processivity for a polymerase used as set forth herein can be, for example, at most 1 million nucleotides, 100,000 nucleotides, 10,000 nucleotides, 1,000 nucleotides, 100 nucleotides or 50 nucleotides. Polymerases can also be characterized according to their rate of processivity or nucleotide incorporation. For example, many native polymerases can incorporate nucleotides at a rate of at least 1,000 nucleotides per second. In some embodiments a slower rate may be desired. For example, an appropriate polymerase and reaction conditions can be used to achieve an average rate of at most 500 nucleotides per second, 100 nucleotides per second, 10 nucleotides per second, 1 nucleotide per second, 1 nucleotide per 10 seconds, 1 nucleotide per minute or slower. As set forth in further detail elsewhere herein, nucleotide analogs can be used that have slower or faster rates of incorporation than naturally occurring nucleotides. It will be understood that polymerases from any of a variety of sources can be modified to increase or decrease their average processivity or their average rate of processivity (e.g. average rate of nucleotide incorporation) or both. Accordingly, a desired reaction rate can be achieved using appropriate polymerase(s), nucleotide analog(s), nucleic acid template(s) and other reaction conditions.

Depending on the embodiment that is to be used, a polymerase can be either thermophilic or heat inactivatable. Thermophilic polymerases are typically useful for high temperature conditions or in thermocycling conditions such as those employed for polymerase chain reaction (PCR) techniques. Examples of thermophilic polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase. Most polymerases isolated from non-thermophilic organisms are heat inactivatable. Examples are DNA polymerases from phage. It will be understood that polymerases from any of a variety of sources can be modified to increase or decrease their tolerance to high temperature conditions. A heat spike (i.e. brief time period of increased temperature) can be used to inactivate one or more heat inactivatable polymerases in an array while leaving thermophilic polymerases in an active state for subsequent reactions or for subsequent cycles of a sequencing reaction.

A polymerase can be attached to a charge sensor using any of a variety of chemistries known in the art. For example, chemical linkers can be used. In many embodiments, the surface of the charge sensor is one of $SiO_2$, $Al_2O_3$, $HfO_2$, $Ta_2O_5$. Other oxides can also be used, for example from the lanthanide group. Nitrides and oxinytrides are also possible. Attachment can conveniently be made through a surface hydroxyl. In particular embodiments, a polymerase (or linker molecule that is attached to a polymerase) includes a functional group. A linker can have a first functional group that interacts with the charge sensor and a second functional group that interacts with the polymerase. Exemplary first functional groups include a pyrene, a benzene, a cyclohexane, and 2,3-dichloro-5,6-dicyano-1,4-benzoquinone. An exemplary second functional group is maleimide. Other chemistries known to covalently link proteins to surfaces or other moieties can be used such as those sold by Thermo Fisher (Waltham, Mass.), or Sigma Aldrich (St. Louis, Mo.). The chemical group on the polymerase attached to the tethers can be thiol, amine or carboxylic group.

A polymerase can be attached to a charge sensor by a non-covalent linkage such as one formed between a receptor and a ligand. Particularly useful linkages are those between streptavidin (or variants or analogs thereof) and biotin (or its analogs), those between complementary nucleic acids, those between antibodies and epitopes and the like.

In some embodiments, a conducting tether is used to attach a polymerase to a charge sensor. Exemplary conducting tethers include those having a structure that includes doped polythiophene, poly(3,4-ethylenedioxythiophene), polyacetylenes, polypyrroles, polyanilines, polyfluorenes, polyphenylenes, polypyrenes, polyazulenes, polynaphthalenes, polycarbazoles, polyindoles, or polyazepines. Charge doping of these tether structures can be achieved by oxidation of the polymer. Exemplary conducting tethers and methods for their creation are set forth in Vernitskaya et al. Russ. Chem. Rev. 66:443ff (1997); MacDiarmid, Angew. Chem., Int. Ed. 40:2581-2590 (2001); or McNeill et al., Aust. J. Chem. 16:1056-75 (1963), each of which is incorporated herein by reference.

In particular embodiments, a solid support can be within or part of a vessel such as a well, tube, channel, cuvette, Petri plate, bottle or the like. A particularly useful vessel is a flow-cell, for example, as described in US 2010/0111768 A1 or Bentley et al., Nature 456:53-59 (2008), each of which is incorporated herein by reference. Exemplary flow-cells are those that are commercially available from Illumina, Inc. (San Diego, Calif.). Flow cells are convenient for delivering bulk reagents to an array of charge sensors during sequencing reactions carried out on the charge sensors. Cyclic processes such as nucleic acid sequencing reactions are particularly well suited for flow cell devices. Another particularly useful vessel is a well in a multiwell plate or microtiter plate.

Nucleic acids used in a method or apparatus of the present disclosure can be composed of DNA, RNA or analogs thereof. The source of the nucleic acids can be genomic DNA, messenger RNA, or other nucleic acids from native sources. In some cases the nucleic acids that are derived from such sources can be amplified prior to use in a method or composition herein. Any of a variety of known amplification techniques can be used including, but not limited to, polymerase chain reaction (PCR), rolling circle amplification (RCA), multiple displacement amplification (MDA), or random prime amplification (RPA). It will be understood that amplification of nucleic acids prior to use in a method or apparatus set forth herein is optional. As such, nucleic acids will not be amplified prior to use in some embodiments of the methods and compositions set forth herein. Nucleic acids can optionally be derived from synthetic libraries. Synthetic nucleic acids can have native DNA or RNA compositions or can be analogs thereof.

Exemplary biological samples from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Target nucleic acids can also be derived from a prokaryote such as a bacterium, *Escherichia coli, staphylococci* or *Mycoplasma pneumoniae*; an archae; a virus such as Hepatitis C virus, ebola virus or human immunodeficiency virus; or a viroid. Nucleic acids can be derived from a homogeneous culture or population of the above organisms or alternatively from a collection of several different organisms, for example, in a community or ecosystem.

Nucleic acids need not be derived from natural sources and can instead be synthesized using known techniques. For example, gene expression probes or genotyping probes can be synthesized and used in the methods and apparatus set forth herein.

In some embodiments, nucleic acids can be obtained as fragments of one or more larger nucleic acids. Fragmentation can be carried out using any of a variety of techniques known in the art including, for example, nebulization, sonication, chemical cleavage, enzymatic cleavage, or physical shearing. Fragmentation may also result from use of a particular amplification technique that produces amplicons by copying only a portion of a larger nucleic acid. For example, PCR amplification produces fragments having a size defined by the length of the nucleotide sequence on the original template that is between the locations where flanking primers hybridize during amplification.

A population of nucleic acids, or amplicons thereof, can have an average strand length that is desired or appropriate for a particular application of the methods or apparatus set forth herein. For example, the average strand length can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for a population of nucleic acids, or amplicons thereof, can be in a range between a maximum and minimum value set forth above.

In some cases a population of nucleic acids can be produced under conditions or otherwise configured to have a maximum length for its members. For example, the maximum length for the members that are used in one or more steps of a method set forth herein or that are present in a particular composition can be less than about 100,000 nucleotides, 50,000 nucleotides, 10,000 nucleotides, 5,000 nucleotides, 1,000 nucleotides, 500 nucleotides, 100 nucleotides or 50 nucleotides. Alternatively or additionally, a population of nucleic acids, or amplicons thereof, can be produced under conditions or otherwise configured to have a minimum length for its members. For example, the minimum length for the members that are used in one or more steps of a method set forth herein or that are present in a particular composition can be more than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The maximum and minimum strand length for nucleic acids in a population can be in a range between a maximum and minimum value set forth above.

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method of nucleic acid sequencing, comprising:
   (a) providing a polymerase attached to a solid support charge sensor;
   (b) contacting the polymerase with a first mixture of nucleotide triphosphates,
       wherein the first mixture comprises different types of nucleotide triphosphates,
       wherein a first two types of the nucleotide triphosphates each are in a same first distinguishable state as one another as compared to a second two types of the nucleotide triphosphates in the first mixture which are not in the first distinguishable state, and
       wherein the polymerase incorporates nucleotides from the nucleotide triphosphates of the first mixture into a nascent strand against a template nucleic acid strand having a sequence;
   (c) detecting the incorporation of nucleotides from the nucleotide triphosphates of the first mixture via the charge sensor,
       wherein the first two types of the nucleotide triphosphates produce signals that are distinguished, based on the first distinguishable state, from signals produced by the second two types of the nucleotide triphosphates in the first mixture,
       thereby acquiring a first signal pattern;
   (d) contacting the polymerase with a second mixture of nucleotide triphosphates,
       wherein the second mixture comprises at least the first two types of nucleotide triphosphates,
       wherein one type of the first two types of the nucleotide triphosphates is in a second distinguishable state as compared to the other type of the first two types of the nucleotide triphosphates in the second mixture,
       wherein the polymerase incorporates nucleotides from the nucleotide triphosphates of the second mixture into a nascent strand against the template nucleic acid;
   (e) detecting the incorporation of nucleotides from the nucleotide triphosphates of the second mixture via the charge sensor,
       wherein the one type of the two types of the nucleotide triphosphates produces a signal that is distinguished, based on the second distinguishable state, from a signal that is produced by the other type of the two types of the nucleotide triphosphates in the second mixture,
       thereby acquiring a second signal pattern that is different from the first pattern; and
   (f) determining the sequence of the template nucleic acid based on differences between the first and second signal patterns.

2. The method of claim 1, wherein the first distinguishable state in step (b) comprises a non-natural moiety that is attached to each type of the first two types of the nucleotide triphosphates.

3. The method of claim 2, wherein the second distinguishable state in step (d) comprises the non-natural moiety that is attached to the one type of the first two types of the nucleotide triphosphates.

4. The method of claim 2, wherein the first distinguishable state comprises a different non-natural moiety in step (b) compared to the second distinguishable state in step (d).

5. The method of claim 1, wherein the first distinguishable state in step (b) comprises a lower quantity or concentration of each type of the first two types of the nucleotide triphosphates compared to the quantity or concentration of each type of the second two types of the nucleotide triphosphates in the first mixture.

6. The method of claim 5, wherein the second distinguishable state in step (d) comprises a lower quantity or concentration of the one type of the first two types of the nucleotide triphosphates compared to the quantity or concentration of the other type of the first two types of the nucleotide triphosphates in the second mixture.

7. The method of claim 1, wherein the template nucleic acid strand is circular.

8. The method of claim 1, wherein the different types of nucleotide triphosphates in the first mixture complement four different nucleotides in the template nucleic acid strand.

9. The method of claim 8, wherein the different types of nucleotide triphosphates in the second mixture complement the four different nucleotides in the template nucleic acid strand.

10. The method of claim 1, wherein the charge sensor is part of an array of charge sensors, whereby step (a) comprises providing a plurality of polymerases each attached to a solid support charge sensor in the array.

11. The method of claim 10, wherein step (b) comprises contacting the polymerases with the first mixture of nucleotide triphosphates; and step (c) comprises detecting the incorporation of the nucleotides via the charge sensors in the array.

12. The method of claim 1, wherein during step (c) the first distinguishable state of the first two types of the nucleotide triphosphates produces a signal change having a polarity that is opposite the polarity in signal change produced by the second two types of nucleotide triphosphates in the first mixture.

13. The method of claim 12, wherein during step (e) the second distinguishable state of the one type of the first two types of the nucleotide triphosphates produces a signal change having a polarity that is opposite the polarity in signal change produced by the other type of the first two types of nucleotide triphosphates in the second mixture.

14. The method of claim 1, wherein during step (c) the first distinguishable state of the first two types of the nucleotide triphosphates produces a delay in signal change compared to the signal change produced by the second two types of the nucleotide triphosphates in the first mixture.

15. The method of claim 14, wherein during step $_f$ the second distinguishable state of the one type of the first two types of the nucleotide triphosphates produces a delay in signal change compared to the signal change produced by the other type of the first two types of nucleotide triphosphates in the second mixture.

16. The method of claim 1, wherein during step (c) the first distinguishable state of the first two types of the nucleotide triphosphates produces an attenuated intensity in signal change compared to the signal change produced by the second two types of the nucleotide triphosphates in the first mixture.

17. The method of claim 16, wherein during step (e) the second distinguishable state of the one type of the first two types of the nucleotide triphosphates produces an attenuated intensity in signal change compared to the signal change produced by the other type of the first two types of nucleotide triphosphates in the second mixture.

18. The method of claim 1, wherein during step (c) the first distinguishable state of the first two types of the nucleotide triphosphates produces an increased intensity in signal change compared to the signal change produced by the second two types of the nucleotide triphosphates in the first mixture.

19. The method of claim 18, wherein during step the second distinguishable state of the one type of the first two types of the nucleotide triphosphates produces an increased intensity in signal change compared to the signal change produced by the other type of the first two types of nucleotide triphosphates in the second mixture.

20. The method of claim 1, wherein during step (c) the first distinguishable state of the first two types of the nucleotide triphosphates produces a prolonged signal change compared to the signal change produced by the second two types of the nucleotide triphosphates in the first mixture.

21. The method of claim 20, wherein during step ig) the second distinguishable state of the one type of the first two types of the nucleotide triphosphates produces a prolonged signal change compared to the signal change produced by the other type of the first two types of nucleotide triphosphates in the second mixture.

22. The method of claim 1, wherein during step (c) the first distinguishable state of the first two types of the nucleotide triphosphates produces a shorter lived signal change compared to the signal change produced by the second two types of the nucleotide triphosphates in the first mixture.

23. The method of claim 22, wherein during step (e) the second distinguishable state of the one type of the first two types of the nucleotide triphosphates produces a shorter lived signal change compared to the signal change produced by the other type of the first two types of nucleotide triphosphates in the second mixture.

24. The method of claim 1, wherein the charge sensor is selected from the group consisting of SWNT FET, nanowire FET, FinFET, trigate FET, tunneling FET, magnetic sensor, electrochemical sensor, and nano electromechanical sensor.

25. The method of claim 24, wherein the charge sensor is the nanowire FET, and the nanowire FET is a silicon nanowire FET.

26. The method of claim 1, wherein the solid support charge sensor is a field-effect transistor including a conducting channel, wherein the conducting channel is a semiconductor.

27. A method of nucleic acid sequencing, comprising:
  (a) contacting a polymerase, which is attached to a solid support charge sensor, with a mixture of nucleotide triphosphates,
    wherein the mixture comprises different types of nucleotide triphosphates,
    wherein a first type of the nucleotide triphosphates includes a non-natural moiety which is not included in the other types of the nucleotide triphosphates in the mixture, and
    wherein the polymerase incorporates nucleotides from the nucleotide triphosphates of the mixture into a nascent strand against a template nucleic acid strand;
  (b) detecting the incorporation of the nucleotides of step (a) via the charge sensor,
    wherein the non-natural moiety of the first type of the nucleotide triphosphates produces a signal that is unique in polarity compared to signals produced by the other types of the nucleotide triphosphates in the mixture.

28. The method of claim 27, wherein:
step (b) acquires a first signal pattern; and
the method further comprises:
  (c) contacting the polymerase with a second mixture of nucleotide triphosphates,
    wherein the second mixture comprises different types of nucleotide triphosphates,
    wherein a second type of the nucleotide triphosphates in the second mixture includes the non-natural moiety which is not included in the other types of nucleotide triphosphates in the second mixture, and wherein the polymerase incorporates nucleotides from the nucleotide triphosphates of the second mixture into a nascent strand against the template nucleic acid strand;
(d) detecting the incorporation of the nucleotides of step (c) via the charge sensor,
wherein the non-natural moiety of the 'second type of the nucleotide triphosphates in the second mixture produces a signal that is unique in polarity compared to signals produced by other types of nucleotide triphosphates in the second mixture,
thereby acquiring a second signal pattern; and
(e) determining the sequence of the template nucleic acid based on differences between the first and second signal patterns.

29. The method of claim 28, further comprising:
(f) contacting the polymerase with a third mixture of nucleotide triphosphates, wherein the third mixture comprises different types of nucleotide triphosphates,
wherein a third type of the nucleotide triphosphates in the third mixture includes the non-natural moiety which is not included in the other types of nucleotide triphosphates in the third mixture, and
wherein the polymerase incorporates nucleotides from the nucleotide triphosphates of the third mixture into a nascent strand against the template nucleic acid strand; and
(g) detecting the incorporation of the nucleotides of step (f) via the charge sensor,
wherein the non-natural moiety of the third type of the nucleotide triphosphates in the third mixture produces a signal that is unique in polarity compared to signals produced by other types of nucleotide triphosphates in the third mixture,
thereby acquiring a third signal pattern;
wherein the sequence of the template nucleic acid further is determined based on the third signal pattern.

30. The method of claim 29, further comprising:
(h) contacting the polymerase with a fourth mixture of nucleotide triphosphates, wherein the fourth mixture comprises different types of nucleotide triphosphates,
wherein a fourth type of the nucleotide triphosphates in the fourth mixture includes the non-natural moiety which is not included in the other types of nucleotide triphosphates in the fourth mixture, and
wherein the polymerase incorporates nucleotides from the nucleotide triphosphates of the fourth mixture into a nascent strand against the template nucleic acid strand; and
(i) detecting the incorporation of the nucleotides of step (h) via the charge sensor,
wherein the non-natural moiety of the fourth type of the nucleotide triphosphates in the fourth mixture produces a signal that is unique in polarity compared to signals produced by other types of nucleotide triphosphates in the fourth mixture,
thereby acquiring a fourth signal pattern;
wherein the sequence of the template nucleic acid further is determined based on the fourth signal pattern.

31. The method of claim 27, wherein the mixture in step (a) comprises a lower quantity or concentration of the first type of the nucleotide triphosphates compared to the quantity or concentration of the other types of the nucleotide triphosphates in the mixture.

32. The method of claim 31, wherein during step (b) the lower quantity or concentration of the first type of the nucleotide triphosphates produces a delay in the signal change compared to the signal change produced by the other types of nucleotide triphosphates in the mixture.

33. The method of claim 27, wherein the template nucleic acid strand is circular.

34. The method of claim 27, wherein the different types of nucleotide triphosphates in the mixture complement four different nucleotides in the template nucleic acid strand.

35. The method of claim 27, wherein the charge sensor is part of an array of charge sensors.

36. The method of claim 27, wherein the charge sensor is selected from the group consisting of SWNT FET, nanowire FET, FinFET, trigate FET, tunneling FET, magnetic sensor, electrochemical sensor, and nanoelectromechanical sensor.

37. The method of claim 36, wherein the charge sensor is the nanowire FET, and the nanowire FET is a silicon nanowire FET.

38. The method of claim 27, wherein the solid support charge sensor is a field-effect transistor including a conducting channel, wherein the conducting channel is a semiconductor.

39. The method of claim 27, wherein the polymerase is covalently attached to the solid support charge sensor.

40. A method of nucleic acid sequencing, comprising:
(a) contacting a polymerase, which is attached to a solid support charge sensor, with a mixture of nucleotide triphosphates,
wherein the mixture comprises different types of nucleotide triphosphates,
wherein a first type of the nucleotide triphosphates produces a signal change having a first polarity and exhibits a first state in nucleotide incorporation kinetics,
wherein a second type of the nucleotide triphosphates produces a signal change having the first polarity and exhibits a second state in nucleotide incorporation kinetics that is faster than the first state,
wherein a third type of the nucleotide triphosphates produces a signal change having a second polarity that is opposite to the first polarity and exhibits the first state in nucleotide incorporation kinetics, and
wherein a fourth type of the nucleotide triphosphates produces a signal change having the second polarity and exhibits the second state in nucleotide incorporation kinetics, and
wherein the polymerase incorporates nucleotides from the mixture into a nascent strand against a template nucleic acid strand;
(b) detecting the incorporation of the nucleotides via the charge sensor,
wherein each of the first, second, third, and fourth types of the nucleotide triphosphates produces a unique signal.

41. The method of claim 40, wherein the charge sensor is selected from the group consisting of SWNT FET, nanowire FET, FinFET, trigate FET, tunneling FET, magnetic sensor, electrochemical sensor, and nano electromechanical sensor.

42. The method of claim 41, wherein the charge sensor is the nanowire FET, and the nanowire FET is a silicon nanowire FET.

43. The method of claim 40, wherein the solid support charge sensor is a field-effect transistor including a conducting channel, wherein the conducting channel is a semiconductor.

44. The method of claim 40, wherein the polymerase is covalently attached to the solid support charge sensor.

* * * * *

UNITED STATES PATENT AND TRADEMARK OFFICE
CERTIFICATE OF CORRECTION

PATENT NO. : 10,787,704 B2
APPLICATION NO. : 15/572741
DATED : September 29, 2020
INVENTOR(S) : Gunderson et al.

Page 1 of 1

It is certified that error appears in the above-identified patent and that said Letters Patent is hereby corrected as shown below:

In the Claims

At Column 23, Line 38, Claim 15, delete "step;" and insert -- step (e) --, therefor.

At Column 23, Line 62, Claim 19, delete "during step the" and insert -- during step (e) the --, therefor.

At Column 24, Line 7, Claim 21, delete "step ig)" and insert -- step (e) --, therefor.

At Column 24, Line 29, Claim 24, delete "nano electromechanical" and insert -- nanoelectromechanical --, therefor.

At Column 25, Line 7, Claim 28, delete "of the `second" and insert -- of the second --.

At Column 26, Line 57, Claim 41, delete "nano electromechanical" and insert -- nanoelectromechanical --.

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*